United States Patent
Simard et al.

(10) Patent No.: US 10,900,040 B2
(45) Date of Patent: Jan. 26, 2021

(54) METHODS OF REDUCING OR PREVENTING INTIMAL DAMAGE CAUSED BY MECHANICAL STIMULATION OF ENDOTHELIAL CELLS

(71) Applicants: University of Maryland, Baltimore, Baltimore, MD (US); The United States of America as Represented by the Department of Veterans Affairs, Washington, DC (US); Biogen Chesapeake, LLC, Cambridge, MA (US)

(72) Inventors: J. Marc Simard, Baltimore, MD (US); Sven Jacobson, New York, NY (US)

(73) Assignees: University of Maryland, Baltimore, Baltimore, MD (US); The United States of America as Represented by the Department of Veterans Affairs, Washington, DC (US); Biogen Chesapeake, LLC, Cambridge, MA (US)

( * ) Notice: Subject to any disclaimer, the term of this patent is extended or adjusted under 35 U.S.C. 154(b) by 41 days.

(21) Appl. No.: 15/577,273

(22) PCT Filed: May 25, 2016

(86) PCT No.: PCT/US2016/034066
§ 371 (c)(1),
(2) Date: Nov. 27, 2017

(87) PCT Pub. No.: WO2016/196113
PCT Pub. Date: Dec. 8, 2016

(65) Prior Publication Data
US 2018/0155727 A1 Jun. 7, 2018

Related U.S. Application Data

(60) Provisional application No. 62/168,589, filed on May 29, 2015.

(51) Int. Cl.
| | | |
|---|---|---|
| *A61P 9/10* | (2006.01) | |
| *A61K 31/64* | (2006.01) | |
| *C12N 15/113* | (2010.01) | |
| *A61K 31/196* | (2006.01) | |
| *A61K 31/132* | (2006.01) | |
| *A61K 31/05* | (2006.01) | |
| *A61P 9/00* | (2006.01) | |
| *A61M 25/10* | (2013.01) | |
| *C07K 14/705* | (2006.01) | |

(52) U.S. Cl.
CPC .......... *C12N 15/1138* (2013.01); *A61K 31/05* (2013.01); *A61K 31/132* (2013.01); *A61K 31/196* (2013.01); *A61K 31/64* (2013.01);

*A61P 9/00* (2018.01); *A61P 9/10* (2018.01); *A61M 25/104* (2013.01); *C07K 14/705* (2013.01); *C12N 2310/11* (2013.01); *C12N 2310/315* (2013.01)

(58) Field of Classification Search
None
See application file for complete search history.

(56) References Cited

U.S. PATENT DOCUMENTS

| | | |
|---|---|---|
| 2001/0009907 A1 | 7/2001 | Martin et al. |
| 2010/0092469 A1* | 4/2010 | Simard ............... A61K 31/56 514/1.1 |
| 2010/0311639 A1 | 12/2010 | Simard |
| 2014/0171467 A1 | 6/2014 | Simard |

OTHER PUBLICATIONS

Novakovic et al, 2012 (Neurology. 79(Suppl 1):S148-S157).*
Bavry et al, 2008. European Heart Journal. 29: 2989-3001.*
Fishman et al., "Adiponectin: a manifold therapeutic target for metabolic syndrome, diabetes, and coronary disease?" Cardiovascular Diabetology, vol. 13, No. 1, Jan. 1, 2014.
Woo et al. "The Sulfonylurea Receptor 1 (Sur1)-Transcient Receptor Potential Melastatin 4 (Trpm4) Channel" The Journal of Biological Chemistry, Feb. 1, 2013, vol. 288, No. 5, pp. 3655-3667.
Tosun et al., "Inhibition or the Sur1-Trpm4 Channel Reduces Neuroinflammation and Cognitive Impairment in Subarachnoid Hemorrhage" Stroke, 2013, vol. 44(12). p. 3522-8.
Mehta et al., "Sur1-Trpm4 Cation Channel Expression in Human Cerebral Infarcts" J. Neuropathol Exp Neurol, Aug. 2015, vol. 74(8), p. 835-49.
Lee et al: "Ghrelin inhibits BSCB disruption/hemorrhage by attenuating MMP-9 and SUR1 /TrpM4 expression and activation after spinal cord injury", Biochimica et Biophysica Acta. Molecular Basis of Disease, vol. 1842, No. 12, Sep. 28, 2014 (Sep. 28, 2014), pp. 2403-2412, Amsterdam, NL.

* cited by examiner

Primary Examiner — Zachary C Howard
(74) Attorney, Agent, or Firm — Norton Rose Fulbright US LLP

(57) ABSTRACT

Embodiments of the disclosure encompass methods and/or compositions for ameliorating or preventing intimal damage caused by mechanical stimulation of endothelial cells. The damage may be caused by use of a device within an artery, vein, or capillary of an individual, such as to remove a thrombus, an embolus or an atherosclerotic plaque in the vessel. Treatment and prevention embodiments concern therapeutically effective amounts of one or more antagonists of the SUR1-TRPM4 channel that is upregulated upon the mechanical stimulation.

9 Claims, 2 Drawing Sheets
Specification includes a Sequence Listing.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
gtgtgcatcg ctgtcccaca                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
ctgcgatagc actcgccaaa                                              20
```

METHODS OF REDUCING OR PREVENTING INTIMAL DAMAGE CAUSED BY MECHANICAL STIMULATION OF ENDOTHELIAL CELLS

This application is a national phase application under 35 U.S.C. § 371 that claims priority to International Application No. PCT/US2016/034066 filed May 25, 2016 which claims priority to U.S. Provisional Patent No. 62/168,589, filed May 29, 2015, all of which are incorporated by reference herein in their entirety.

TECHNICAL FIELD

Embodiments of the disclosure concern at least the fields of cell biology, molecular biology, and medicine.

BACKGROUND

The present disclosure addresses a long-felt need in the art to provide a method for reducing or preventing intimal damage in vessels of individuals upon mechanical stimulation of endothelial cells therein.

BRIEF SUMMARY

In embodiments of the disclosure, the SUR1-TRPM4 channel (which also may be referred to as the $NC_{Ca\text{-}ATP}$ channel) is upregulated in endothelial cells by mechanical stimulation. Such upregulation may result in deleterious physiological effects in the affected cells, tissues, and/or organs, and the present disclosure provides methods to avoid such processes or treat medical conditions that are directly or indirectly caused by them. In specific embodiments, one or more antagonists of the channel prevents the upregulation of one or more channel components or reduces the upregulation of one or more channel components.

Compounds acting on sulfonylurea receptor 1 (SUR1) and/or transient receptor potential cation channel, subfamily M, member 4 (TRPM4) can be used to prevent and/or reduce and/or treat intimal damage caused directly or indirectly by mechanical stimulation of endothelial cells. Such mechanical stimulation can take place during (and/or after) any endovascular procedure, for example catheter angiography, mechanical thrombectomy, endovascular aneurysm repair, etc.

BRIEF DESCRIPTION OF THE FIGURES

FIGS. 1A and 1C: Immunofluorescent labeling for the NF-kappaB subunit, p65, and nuclear stain with DAPI (blue), under control conditions (FIG. 1A, left panel) and 5 min after mechanical stimulation (FIG. 1A, right panel), showing prominent nuclear translocation of p65; quantification showed a strong increase in p65 nuclear translocation in ~80% of the cells (FIG. 1C, left); , P<0.01. FIGS. 1B and 1C: Immunofluorescent labeling of endothelial cells for TRPM4 6 hours after mechanical stimulation revealed prominent upregulation of TRPM4 (FIG. 1B), and a 6-fold increase in the number of TRPM4-expressing cells (FIG. 1C, right); , P<0.01. These data are consistent with mechanical stimulation causing transcriptional upregulation of channel subunits via activation of the mechanosensitive transcription factor, NF-kappaB.

FIG. 2A: Patch clamp recordings demonstrated functional SUR1-TRPM4 channel currents, with the following characteristic features of: (i) channel currents carried by Cs+ ions; (ii) channel opening induced by ATP depletion (using sodium azide plus 2-deoxyglucose): (iii) channel blockade by N-methyl-D-glucamine (NMDG). FIG. 2B: Amplitudes of SUR1-TRPM4 channel currents measured at −50 mV under control conditions before mechanical activation (CTR), following mechanical activation (STR), following mechanical activation in the presence of the NF-kappaB inhibitor, pyrrolidine dithiocarbamate (PDTC) as negative control, and without mechanical activation, in the presence of tumor necrosis factor alpha (TNFalpha), as positive control. These data confirm the critical role of the mechanosensitive transcription factor, NF-kappaB, in SUR1-TRPM4 channel upregulation.

DETAILED DESCRIPTION

I. Exemplary Definitions

Figure 1A:
FIGS. 1A, 1B, and 1C. Mechanical stimulation of endothelial cells causes NFkappaB activation and upregulation of TRPM4. Endothelial cells were cultured in dishes with flexible bottoms and the cells were mechanically stimulated by applying puffs of air to the underside of the dishes.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternative are mutually exclusive, although the disclosure supports a definition that refers to only alternatives and "and/or."

As used herein, the term "antagonist" refers to a biological or chemical agent that acts within the body to reduce the physiological activity of another chemical or biological substance. In the present invention, the antagonist blocks, inhibits, reduces and/or decreases the activity of a SUR1-TRPM4 channel of an endothelial cell (e.g., vasculature endothelial cells). In the present invention, the antagonist combines, binds, or associates with a SUR1-TRPM4 channel of an endothelial cell (e.g., vasculature endothelial cells), such that the SUR1-TRPM4 channel is closed (deactivated), meaning reduced biological activity with respect to the biological activity in the diseased state. In certain embodiments, the antagonist combines, binds and/or associates with a regulatory subunit of the SUR1-TRPM4 channel, particularly a SUR1. Alternatively, the antagonist combines, binds, and/or associates with a pore-forming subunit of the SUR1-TRPM4 channel, particularly TRPM4, such that the SUR1-TRPM4 channel is closed (deactivated). The terms antagonist or inhibitor can be used interchangeably.

The term "preventing" as used herein refers to minimizing, reducing or suppressing the risk of developing a disease state or parameters relating to the disease state or progression or other abnormal or deleterious conditions.

II. General Embodiments

In particular embodiments, treatment is provided to an individual in need thereof who is going to be exposed to and/or is exposed to and/or will be exposed to treatment that will cause or has the potential of causing intimal damage, in particular in any type of blood vessel in the individual.

Examples of Methods that May Cause Intimal Damage

In some embodiments, methods that may cause intimal damage can be of any kind, and the intimal damage may occur in any kind of vasculature of a mammal. In specific embodiments, the damage occurs or has the potential of occurring in a blood vessel of any kind, including an artery or vein or capillary or a combination thereof. In particular embodiments, the intimal damage can occur by one or more mechanical treatments in which a device is exposed to the intima, either transiently or permanently. The device may or may not be used because of the presence of a clot (or a thrombus or embolus or atherosclerotic plaque) in a vessel, and the clot may be located anywhere in the individual, including in the brain, heart, appendage, bowel, muscle, lungs, and so forth. In specific embodiments, a clot is removed not by a device but by a drug, such as tPA, for example.

In particular embodiments, the methods and/or compositions of the disclosure are employed for cardiovascular applications. In specific embodiments, damage to vascular endothelial cells is prevented after introduction of a stent into a coronary or carotid artery or a peripheral blood vessel in a limb, for example.

In certain embodiments, mechanical treatments include the use of catheters to directly deliver a clot-disrupting or clot retrieval device to a thromboembolus that is occluding a cerebral artery. Most devices are used in cerebral vessels that are 2-5 mm. Mechanical thrombolytic/thrombectomy devices can remove a clot in a matter of minutes. The MERCI retrieval system (Concentric Medical, Mountain View, Calif., USA) was the first device to be approved for intracranial thrombectomy. The device comprises a corkscrew shaped nitinol coil that engages the thrombus during thrombectomy.

The Penumbra device was specifically designed for vessel recanalization in acute stroke using a debulking and aspiration technique followed by direct thrombus extraction if clot remains.

Self expanding stent implantation allows almost immediate restoration of blood flow by thrombus entrapment between the stent struts and the vessel wall.

The most recently developed devices, known as stentrievers, have shown higher recanalization rates and better outcomes than those seen with the older devices, for example the Merci Retriever® and Penumbra devices. In addition to conventional stenting, stent retrievers allow thrombectomy to be performed by pulling back the deployed stent into the guide catheter, whereby the struts of the stent engage the thrombotic material. Particularly advantageous is that the stent is applicable repeatedly and can be used even in small peripheral vessel branches. In contrast with conventional stent systems, stent retrievers require no anticoagulation or antiaggregation treatment as the stent is not deployed permanently.

In the case of stent retrievers, the intervention is performed under general anesthesia or conscious sedation. A 6-8 Fr guide catheter is placed into the target artery using transfemoral access. To prevent distal thrombus migration and to enhance aspiration during thrombectomy, several groups and manufacturers recommend using a balloon guide catheter for this purpose. A flexible 5-6 F catheter can be used as an intermediate catheter to gain distal access close to the occluded segment. The thrombus is crossed with a 0.021 inch or a 0.027 inch microcatheter. Angiographic runs should be performed through the microcatheter to document the proper position of the microcatheter tip distal to the thrombus and to estimate the length of the clot. The stent retriever is subsequently released by pulling back the microcatheter while holding the retriever device in place. The stent retriever should cover the entire length of the occlusion in order to achieve flow restoration when the stent opens. The device is slowly retrieved together with the microcatheter under continuous aspiration through the guide catheter or the intermediate catheter. In case a proximal balloon catheter is used, the balloon is temporarily inflated to block antegrade flow. The maneuver can be repeated several times to achieve complete clot removal. Intraarterial rtPA may also be administered. In the case of ischemic stroke, use of a thrombectomy device may occur well beyond the time window for administration of tPA, for example beyond about 4.5 hours, beyond 6 hours, beyond 8 hours, beyond 10 hours, beyond 12 hours, or even up to 24 hours after onset of stroke. In such cases, treatment with a Sur1-Trpm4 antagonist (an antagonist that inhibits Sur1, Trpm4, or both) would begin after, for example, about 4.5 hours, beyond 6 hours, beyond 8 hours, beyond 10 hours, beyond 12 hours, or even up to 24 hours after onset of stroke.

In the case of ischemic stroke, use of a thrombectomy device may occur well beyond the time window for typical administration of a Sur1-Trpm4 inhibitor for stroke, for example beyond about 4.5 hours, beyond 6 hours, beyond 8 hours, beyond 10 hours, beyond 12 hours, or even up to 24 hours after onset of stroke. In such cases, treatment with a Sur1-Trpm4 antagonist would begin after, for example, about 4.5 hours, beyond 6 hours, beyond 8 hours, beyond 10 hours, beyond 12 hours, or even up to 24 hours after onset of stroke.

III. Methods of Treatment

In particular embodiments, methods of treatment are employed to treat intimal damage caused by a device utilized within a vessel and in which case there is upregulation of expression of one or more components of the SUR1-TRPM4 channel in endothelial cells of the vessel.

In certain embodiments, the procedure that may include a device that causes intimal damage caused by mechanical stimulation includes diagnostic angiograms of any type of organ (including the brain, heart, etc.). In certain embodiments, the procedure concerns intra-arterial therapies in any organ including: thrombectomy (removal of a thrombus or embolus) to restore blood flow; angioplasty to enlarge a vessel constricted by atheroma or by vasospasm; stenting to buttress open a vessel after angioplasty; coiling, stent/coiling, or placing flow diverters for treatment of an aneurysm, and so forth. All of these procedures may induce mechanical stimulation of the endothelium and put an individual at risk for intimal dissection and other consequences of endothelial injury.

When mechanical thrombectomy devices (for example) are used to remove blood clots (in ischemic stroke as well as limb ischemia), the device is advanced through an artery to get to the blood clot. Mechanical stimulation of the endothelial cells occurs during this advancement, during the clot removal, and during the clot and device retrieval, and such mechanical stimulation causes upregulation of the channel.

In some embodiments, for methods that involve invasion of a blood vessel of a mechanical device, the channel may already be upregulated in some cells of the vessel (such as an artery), and this mechanical stimulation may cause further upregulation (exacerbated upregulation). In some embodiments, the upregulation of the SUR1-TRPM4 channel is new and not present before the mechanical stimulation. In particular embodiments, such exacerbated upregulation or new upregulation caused by mechanical causes is entirely separate to the upregulation of SUR1-TRPM4 caused by a stroke or occluded artery itself, or any damage that rtPA may cause in strokes where no mechanical thrombectomy is used. The result of this upregulation of the SUR1-TRPM4 channel upregulation is that endothelial cells may become dysfunctional, or may become more dysfunctional than they would have otherwise. Dysfunction in turn leads to blood brain barrier disruption, edema, hemorrhage, and/or even dissection of the intima (intimal dissection) in large arteries (e.g. M1, M2, M3 and internal/external carotid arteries), for example. By preventing and/or reducing and/or treating damage to these endothelial cells by closing open SUR1-TRPM4 channels or keeping closed SUR1-TRPM4 channels closed, such device-enabled endothelial dysfunction, edema, hemorrhage and/or intimal dissection can be avoided or ameliorated. By avoiding or ameliorating the aforementioned, additional damage to neurons, astrocytes and the tissue and/or organ (such as the brain, heart, bowel, lung, and/or limb, etc.) in general can be avoided (it is well known that edema, hemorrhage and dissection can contribute to additional damage and lesion growth as well as new ischemic lesion in areas of the brain that would otherwise not have been damaged).

When a thrombectomy device is used, in some instances, the diagnosis of stroke (for cases in the brain) and presence of a clot is first performed using CTA, MRA, MRI, CTP, or CT, or a combination of these; diagnosis of the presence of the clot may occur from angiogram, ultrasound, venography, CT scan, a combination thereof, and so forth. In such cases, the diagnosis could first be performed prior to administering the SUR1-TRPM4 antagonist or could be performed after administering the SUR1-TRPM4 antagonist. Monitoring of the presence or state of the occlusion may occur over the course of a particular period of time.

Treatment with SUR1-TRPM4 antagonist in the case of a procedure that may cause mechanical stimulation may occur after the stroke and then either prior to, during, and/or after thrombectomy. Treatment with SUR1-TRPM4 antagonist in the case if mechanical thrombectomy may occur after the stroke and then either prior to, during, and/or after thrombectomy.

When catheter angiography is performed, a device is advanced through the vasculature. Mechanical stimulation of the endothelial cells occurs during this advancement and withdrawal, which causes upregulation of the channel. In some cases the channel may already be upregulated in some cells of the artery, and this mechanical stimulation may cause further upregulation (exacerbated upregulation). In some cases, the upregulation may be new. The result of this upregulation of the SUR1-TRPM4 channel upregulation is that endothelial cells may become dysfunctional, which in turn leads to edema, hemorrhage, and even intimal dissection in large arteries (e.g., M1, M2, M3 and internal/external carotid arteries). By preventing and/or reducing and/or treating damage to these endothelial cells by closing open SUR1-TRPM4 channels or keeping closed SUR1-TRPM4 channels closed, such device-enabled endothelial dysfunction, edema, hemorrhage and/or intimal dissection can be avoided or ameliorated. By avoiding or ameliorating the aforementioned, additional damage to neurons, astrocytes and the brain in general can be avoided (it is well known that edema, hemorrhage and intimal dissection can contribute to additional damage and lesion growth as well as new ischemic lesions in areas of the brain that would otherwise not have been damaged).

In other embodiments, chemical stimulation (with or without concomitant mechanical stimulation) of the intima results in upregulation of the SUR1-TRPM4 channel in endothelial cells of the intima. Such chemical stimulation may or may not be from a compound that has been administered to an individual for the purpose of targeting an occlusion in a blood vessel in the individual.

IV. Pharmaceutical Formulations

The SUR1-TRPM4 antagonist can be administered through any means e.g. orally, intravenously, nasally, transdermally, intraperitoneally, etc. In specific embodiments, the administration route is intravenously. In one example, the SUR1-TRPM4 antagonist is a SUR1 antagonist, for example a sulfonylurea, for example glyburide. In one specific example, the formulation of glyburide is as described by Jacobson (U.S. Pat. No. 8,277,845, which is incorporated by reference herein). In another example the administration method and dosing is as described by Jacobson (U.S. Pat. No. 8,946,293, which is incorporated by reference herein). Other administration and dosing regimens can also be used. Administration can be started before, after, or during a particular procedure, such as a thrombectomy, angiography, insertion of a stent, or angiography, for example. Administration may occur before, during, or after treatment with one or more clot-busting drugs in the absence of a thrombectomy, although in some cases the individual has received, will receive, or is receiving a thrombectomy. In one instance, administration of the SUR1-TRPM4 antagonist would be performed intraarterially before, during, and/or after the endovascular procedure in order to specifically target endothelium in the artery on which endovascular therapy is performed and/or to increase concentrations of the SUR1-TRPM4 antagonist in the target vessel without significantly increasing systemic concentrations. Such intraarterial administration could be the sole administration of a drug acting on SUR1-TRPM4, or could be performed prior, during and/or after another route of administration of a SUR1-TRPM4 antagonist such as, for example intravenous administration.

In some embodiments, an effective amount of an antagonist of SUR1-TRPM4 channel that may be administered to a cell includes a dose of about 0.0001 nM to about 2000 µM. More specifically, doses of an agonist to be administered are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000 µM; about 1000 µM to about 1500 µM and about 1500 µM to about 2000 µM. Of course, all of these amounts are exemplary, and any amount in-between these points is also expected to be of use in the invention.

In certain embodiments, an effective amount of an agonist and/or antagonist of the SUR1-TRPM4 channel or related-compounds thereof as a treatment varies depending upon the host treated and the particular mode of administration. In one embodiment of the invention the dose range of the agonist and/or antagonist of the SUR1-TRPM4 channel or related-compounds thereof will be about 0.01 µg/kg body weight to about 20,000 µg/kg body weight. The term "body weight" is applicable when an animal is being treated. When isolated cells are being treated, "body weight" as used herein should read to mean "total cell body weight". The term "total body weight" may be used to apply to both isolated cell and animal treatment. All concentrations and treatment levels are expressed as "body weight" or simply "kg" in this application are also considered to cover the analogous "total cell body weight" and "total body weight" concentrations. However, those of skill will recognize the utility of a variety of dosage range, for example, 0.01 µg/kg body weight to 20,000 µg/kg body weight, 0.02 µg/kg body weight to 15,000 µg/kg body weight, 0.03 µg/kg body weight to 10,000 µg/kg body weight, 0.04 µg/kg body weight to 5,000 µg/kg body weight, 0.05 µg/kg body weight to 2,500 µg/kg body weight, 0.06 µg/kg body weight to 1,000 µg/kg body weight, 0.07 µg/kg body weight to 500 µg/kg body weight, 0.08 µg/kg body weight to 400 µg/kg body weight, 0.09 µg/kg body weight to 200 µg/kg body weight or 0.1 µg/kg body weight to 100 µg/kg body weight. Further, those of skill will recognize that a variety of different dosage levels will be of use, for example, 0.0001 µg/kg, 0.0002 µg/kg, 0.0003 µg/kg, 0.0004 µg/kg, 0.005 µg/kg, 0.0007 µg/kg, 0.001 µg/kg, 0.1 µg/kg, 1.0 µg/kg, 1.5 µg/kg, 2.0 µg/kg, 5.0 µg/kg, 10.0 µg/kg, 15.0 µg/kg, 30.0 µg/kg, 50 µg/kg, 75 µg/kg, 80 µg/kg, 90 µg/kg, 100 µg/kg, 120 µg/kg, 140 µg/kg, 150 µg/kg, 160 µg/kg, 180 µg/kg, 200 µg/kg, 225 µg/kg, 250 µg/kg, 275 µg/kg, 300 µg/kg, 325 µg/kg, 350 µg/kg, 375 µg/kg, 400 µg/kg, 450 µg/kg, 500 µg/kg, 550 µg/kg, 600 µg/kg, 700 µg/kg, 750 µg/kg, 800 µg/kg, 900 µg/kg, 1 mg/kg, 5 mg/kg, 10 mg/kg, 12 mg/kg, 15 mg/kg, 20 mg/kg, and/or 30 mg/kg.

The channel can be inhibited by a SUR1-TRPM4 channel inhibitor, a SUR1-TRPM4 channel blocker, a type 1 sulfonylurea receptor (SUR1) antagonist, SUR1 inhibitor, a TRPM4 antagonist, a TRPM4 inhibitor, or a compound capable of reducing the magnitude of membrane current through the channel. In specific embodiments, the antagonist of the channel indirectly or directly binds any component of the channel. In particular embodiments, the SUR1 antagonist is selected from the group consisting of glibenclamide, tolbutamide, repaglinide, nateglinide, meglitinide, LY397364, LY389382, glyclazide, glimepiride, estrogen, estrogen related-compounds (estradiol, estrone, estriol, genistein, non-steroidal estrogen (e.g., diethystilbestrol), phytoestrogen (e.g., coumestrol), zearalenone, etc.), MgADP, chloropramide, glipizide, tolazamide, Glibornuride, Gliquidone, Glisoxepide, Glyclopyramide, glimepiride, JB558, JB253, or any compound with a central S-phenylsulfonylurea structure with a p-substituent on the phenyl ring (R) and various groups terminating the urea N' end group

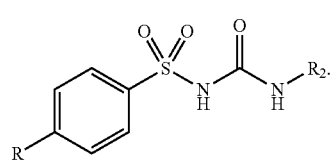

Sulfonylurea group SO$_2$NHONH

In specific embodiments, the SUR1 antagonist is capable of inhibiting or blocking K$_{ATP}$ channels.

In certain embodiments of the invention, antagonists of TRPM4 are employed in methods and/or compositions. Antagonists may be of any kind, but in particular embodiments the antagonists are proteins, nucleic acids, small molecules, and so forth. In specific cases, the TRPM4 antagonists comprise flufenamic acid and/or 9-phenanthrol and/or spermine and/or decavanadate and/or BTP2 and/or anti-TRPM4 antibodies. In specific cases, the TRPM4 nucleic acid antagonists comprises RNAi, such as siRNA or shRNA or antisense oligodeoxynucleotides (AS-ODN). A pair of AS-ODNs found to be highly effective in reducing TRPM4 expression and in improving outcome from spinal cord injury when used together, have the following sequences: (TRPM4-AS1: 5'-GTGTGCATCGCTGTCC-CACA-3' (SEQ ID NO:1); and TRPM4-AS2: 5'-CTGCGA-TAGCACTCGCCAAA-3' (SEQ ID NO:2); sense (SE) or antisense (AS) oligodeoxynucleotides (ODN) were administered that were phosphorothioated to protect from endogenous nucleases.

In certain embodiments, the modulator can be a compound (protein, nucleic acid, siRNA, etc.) that modulates transcription and/or translation of SUR1 (regulatory subunit) and/or the molecular entities that comprise the pore-forming subunit, TRPM4.

In specific embodiments, antisense molecules, RNA interference molecules, siRNA molecules, miRNA molecules, and so forth may be employed to target SUR1 and/or TRPM4.

Pharmaceutical compositions of the present invention comprise an effective amount of one or more modulators of SUR1-TRPM4 channel (antagonist and/or agonist) or related-compounds or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one modulators of SUR1-TRPM4 channel (antagonist and/or agonist) or related-compounds or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The modulators of SUR1-TRPM4 channel (antagonist and/or agonist) or related-compounds may comprise different types of carriers depending on whether it is to be administered in solid, liquid or aerosol form, and whether it need to be sterile for such routes of administration as injection. The present invention can be administered intravenously, intradermally, transdermally, intrathecally, intraventricularly, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The modulators of SUR1-TRPM4 channel (antagonist and/or agonist) or related-compounds may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include modulators of SUR1-TRPM4 channel (antagonist and/or agonist) or related-compounds, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the modulators of SUR1-TRPM4 channel (antagonist and/or agonist) or related-compounds may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic and/or prophylatic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Embodiments Including Thrombolytic Agents

In specific embodiments, methods and/or compositions of the disclosure are provided to an individual that is being subjected to a thrombectomy. In such cases, the individual who will receive and/or who is receiving and/or who has received the thrombectomy may not have responded to treatment with one or more thrombolytic agents, such as intravenous tPA, for example. In particular embodiments, the individual who will receive and/or who is receiving and/or who has received the thrombectomy is also provided one or more thrombolytic agents, such as intraarterial tPA, for example.

V. Kits of the Disclosure

Any of the compositions described herein may be comprised in a kit. In a non-limiting example, it is envisioned that a compound that selectively binds to SUR1 and/or TRPM4 may be comprised in a kit. Such compounds can include, but are not limited to, antibodies (monoclonal or polyclonal), oligonucleotides, polypeptides, small molecule or combinations thereof, antagonist, agonist, etc. It is envisioned that any of these compounds may be linked to a radioactive substance and/or a fluorescent marker and/or an enzymatic tag for quick determination. The kits may also comprise, in suitable container means a lipid, and/or an additional agent, for example a radioactive or enzymatic or fluorescent marker.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the SUR1 and/or TRPM4 antagonist, and any other reagent containers in close confinement for commercial sale. Such containers may include injection or blow molded plastic containers into which the desired vials are retained.

Therapeutic kits of the present invention are kits that may comprise an antagonist, agonist or a related-compound thereof. Depending upon the condition and/or disease that is being treated, the kit may comprise an SUR1 and/or TRPM4 antagonist or related-compound thereof to block and/or inhibit the SUR1-TRPM4 channel. Such kits will generally contain, in suitable container means, a pharmaceutically acceptable formulation of SUR1 and/or TRPM4 antagonist or related-compound thereof. The kit may have a single container means, and/or it may have distinct container means for each compound.

When the components of the kit are provided in one and/or more liquid solutions, the liquid solution is an aqueous solution, with a sterile aqueous solution being particularly preferred. The SUR1 and/or TRPM4 antagonist or related-compounds thereof may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

Examples of aqueous solutions include, but are not limited to ethanol, DMSO and/or Ringer's solution. In certain embodiments, the concentration of DMSO or ethanol that is used is no greater than 0.1% or (1 ml/1000 L).

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the SUR1 antagonist, agonist or related-compounds thereof is suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the SUR1 antagonist, agonist or related-compounds thereof within the body of an animal. Such an instrument may be a syringe, pipette, forceps, and/or any such medically approved delivery vehicle. In specific embodiments, the device that may directly or indirectly cause mechanical stimulation of the endothelial cells may be comprised in the same kit as the SUR1 and/or TRPM 4 antagonist.

In addition to the SUR1 and/or TRPM4 antagonist or related-compounds thereof, the kits may also include a second active ingredient. Examples of the second active ingredient include substances to prevent hypoglycemia (e.g., glucose, D5W, glucagon, etc.), thrombolytic agents, anticoagulants, antiplatelets, statins, diuretics, vasodilators, etc. These second active ingredients may be combined in the same vial as the SUR1 and/or TRPM4 antagonist, agonist or related-compounds thereof or they may be contained in a separate vial.

Still further, the kits of the present invention can also include glucose testing kits. Thus, the blood glucose of the patient is measured using the glucose testing kit, then the SUR1 antagonist, agonist or related-compounds thereof can be administered to the subject followed by measuring the blood glucose of the patient.

In addition to the above kits, the therapeutic kits of the present invention can be assembled such that an IV bag comprises a septum or chamber which can be opened or broken to release the compound into the IV bag. Another type of kit may include a bolus kit in which the bolus kit comprises a pre-loaded syringe or similar easy to use, rapidly administrable device. An infusion kit may comprise the vials or ampoules and an IV solution (e.g., Ringer's solution) for the vials or ampoules to be added prior to infusion. The infusion kit may also comprise a bolus kit for a bolus/loading dose to be administered to the subject prior, during or after the infusion.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Upregulation of SUR1-TRPM4 Channel Upon Mechanical Stimulation

Figure 1B:
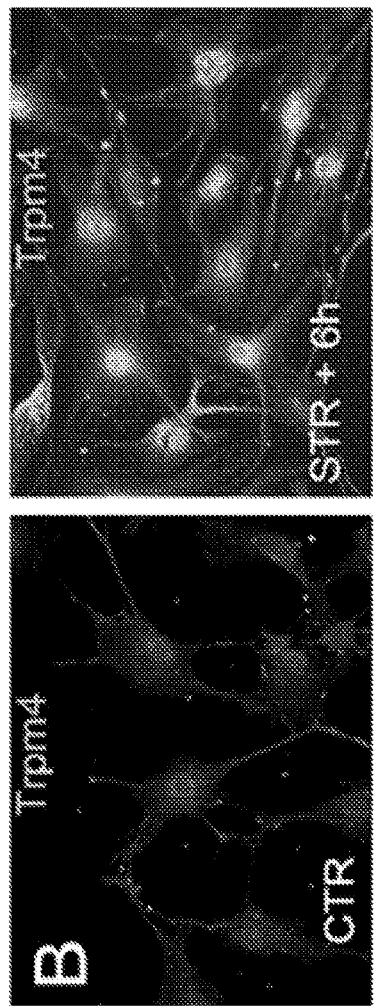
Figure 1C:
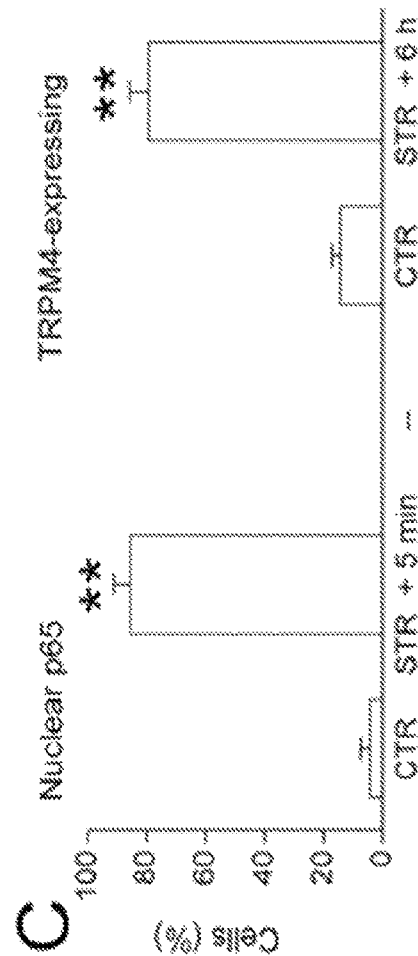
Figure 2A:
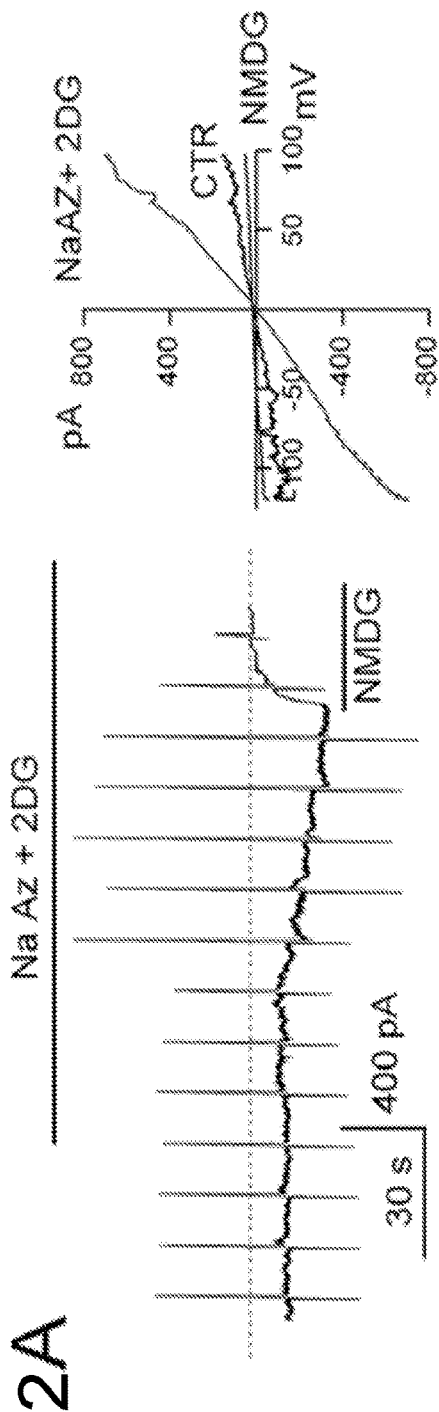
FIGS. 2A and 2B. Mechanical stimulation of endothelial cells causes upregulation of functional SUR1-TRPM4 channels. Endothelial cells were cultured in dishes with flexible bottoms and the cells were mechanically stimulated by applying puffs of air to the underside of the dishes.
Figure 2B:
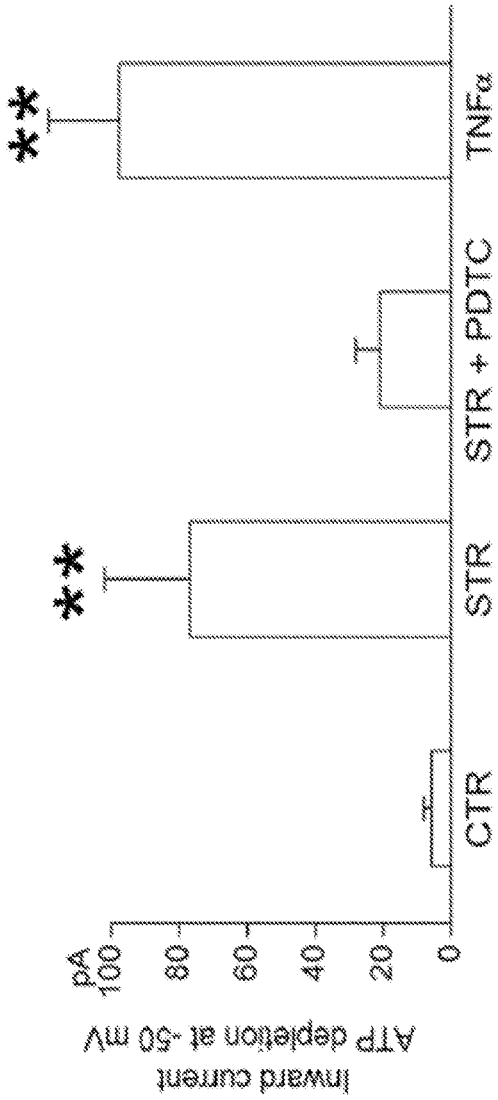

Endothelial cells were cultured in dishes with flexible bottoms and the cells were mechanically stimulated by applying puffs of air to the underside of the dishes. Mechanical stimulation resulted in activation of the mechanosensitive transcription factor, NF-κB, resulting in rapid (5 minutes) nuclear translocation of the NF-κB subunit, p65 (FIGS. 1A and 1C). NFκB activation caused robust transcriptional upregulation of the SUR1-TRPM4 channels 6 hours later (FIGS. 1B and 1C). Patch clamp recordings confirmed the upregulation of functional SUR1-TRPM4 channels, which exhibited the characteristic features of channel opening induced by ATP depletion (using sodium azide plus 2-deoxyglucose), and channel blockade by N-methyl-D-glucamine (NMDG) (FIG. 2A). The critical role of the mechanosensitive transcription factor, NF-κB, in Sur1-Trpm4 channel upregulation was confirmed using the NF-κB inhibitor, pyrrolidine dithiocarbamate (PDTC) as negative control, and the NF-κB activator, tumor necrosis factor α (TNFα), as positive control (FIG. 2B).

Thus, in embodiments of the disclosure, drugs acting on SUR1 and/or TRPM4 can be used to prevent and/or reduce and/or treat intimal damage caused by mechanical stimulation of endothelial cells. Such mechanical stimulation can take place during any endovascular procedure, for example catheter angiography, mechanical thrombectomy, endovascular aneurysm repair, etc.

The foregoing has outlined rather broadly the features and technical advantages of the present invention in order that the detailed description of the invention that follows may be better understood. Additional features and advantages of the invention will be described herein which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

We claim:

1. A method of inhibiting or reducing intimal damage caused by advance of a catheter through vasculature of a subject in need thereof comprising administering a therapeutically effective amount of glibenclamide or a pharmaceutically acceptable salt thereof to the subject, wherein the administering is solely local administration to increase local concentrations of the glibenclamide or pharmaceutically acceptable salt thereof in a blood vessel undergoing advance of the catheter.

2. The method of claim 1, wherein the advance of a catheter through vasculature of the subject is during catheter angiography.

3. The method of claim 1, wherein the advance of a catheter through vasculature of the subject causes endothelial dysfunction in a blood vessel of the subject.

4. The method of claim 1, wherein the advance of a catheter through vasculature of the subject causes edema in a blood vessel of the subject.

5. The method of claim 1, wherein the advance of a catheter through vasculature of the subject causes hemorrhage in a blood vessel of the subject.

6. The method of claim 1, wherein the advance of a catheter through vasculature of the subject causes intimal dissection in arteries of the subject.

7. The method of claim 1, wherein the advance of a catheter through vasculature of the subject is during a thrombectomy procedure.

8. The method of claim 1, wherein the subject is undergoing or has undergone a procedure to remove or disrupt a thrombus or embolus or atherosclerotic plaque in a blood vessel.

9. The method of claim 1, wherein the subject is undergoing or has undergone a endovascular aneurysm repair procedure.

* * * * *